United States Patent
Strong

(10) Patent No.: US 9,046,454 B2
(45) Date of Patent: Jun. 2, 2015

(54) PROCESSING OF ANALYTE SUPPORTS WITH OSCILLATING FLUID BY INTERRUPTED ROTATION

(75) Inventor: William Strong, El Cerrito, CA (US)

(73) Assignee: Bio-Rad Laboratories, Inc., Hercules, CA (US)

(*) Notice: Subject to any disclaimer, the term of this patent is extended or adjusted under 35 U.S.C. 154(b) by 108 days.

(21) Appl. No.: 13/491,209

(22) Filed: Jun. 7, 2012

(65) Prior Publication Data
US 2013/0143209 A1 Jun. 6, 2013

Related U.S. Application Data

(60) Provisional application No. 61/494,748, filed on Jun. 8, 2011.

(51) Int. Cl.
| | | |
|---|---|---|
| *B01L 3/00* | (2006.01) | |
| *G01N 1/28* | (2006.01) | |
| *G01N 1/30* | (2006.01) | |
| *B01L 9/00* | (2006.01) | |
| *G01N 1/31* | (2006.01) | |
| *G01N 21/07* | (2006.01) | |

(52) U.S. Cl.
CPC .. *G01N 1/28* (2013.01); *G01N 1/30* (2013.01); *B01L 9/52* (2013.01); *B01L 9/527* (2013.01); *B01L 2300/0806* (2013.01); *B01L 2300/0803* (2013.01); *B01L 2400/0409* (2013.01); *G01N 1/31* (2013.01); *B01L 3/50273* (2013.01); *G01N 21/07* (2013.01)

(58) Field of Classification Search
CPC ............... B01L 2300/0806; B01L 2400/0409; B01L 2300/0887; B01L 2300/0864; B01L 2300/0803; G01N 35/00069; G01N 21/07
See application file for complete search history.

(56) References Cited

U.S. PATENT DOCUMENTS

| | | |
|---|---|---|
| 4,702,266 A | 10/1987 | Chu |
| 4,913,791 A | 4/1990 | Hurd et al. |
| 5,234,559 A | 8/1993 | Collier et al. |
| 5,580,790 A | 12/1996 | Wall et al. |
| 6,843,593 B2 | 1/2005 | Perez et al. |
| 7,749,369 B2 | 7/2010 | Kumar et al. |
| 2002/0020679 A1 | 2/2002 | Jorgensen et al. |
| 2005/0191620 A1 | 9/2005 | McDevitt et al. |
| 2007/0128708 A1* | 6/2007 | Gamelin ............... 435/173.6 |
| 2008/0152546 A1* | 6/2008 | Bedingham et al. ......... 422/103 |
| 2009/0023610 A1* | 1/2009 | Peytavi ........................ 506/39 |
| 2009/0317896 A1* | 12/2009 | Yoo ............................ 435/287.1 |
| 2010/0120129 A1 | 5/2010 | Amshey et al. |

FOREIGN PATENT DOCUMENTS

WO    WO 2010041010 A1 *   4/2010

OTHER PUBLICATIONS

International Search Report and Written Opinion for PCT/US12/41650, 13 pages, mailed Aug. 28, 2012.

* cited by examiner

*Primary Examiner* — Melanie Y Brown
*Assistant Examiner* — Erik B Crawford
(74) *Attorney, Agent, or Firm* — Kilpatrick Townsend and Stockton LLP

(57) ABSTRACT

Analyte supports such as Western blots, gels, and the like is processed for purposes of detection and analysis, by placing the blot or gel on a plate and causing process fluids to oscillate across the blot or gel by intermittently rotating the plate. The plate can be inclined or flat, divided into sectors to accommodate multiple sheets, and multiple plates can be mounted to a single rotating shaft to process a large number of blots or gels simultaneously under the same protocol.

22 Claims, 5 Drawing Sheets

PROCESSING OF ANALYTE SUPPORTS WITH OSCILLATING FLUID BY INTERRUPTED ROTATION

CROSS-REFERENCE TO RELATED APPLICATION

This application claims the benefit of U.S. Provisional Patent Application No. 61/494,748, filed Jun. 8, 2011, the contents of which are incorporated herein by reference in their entirety.

BACKGROUND OF THE INVENTION

1. Field of the Invention

This invention resides in the field of processing of biological samples for analysis of the samples and identification of their components, with a particular focus on the process of transfer membranes for the detection of analytes on the membranes.

2. Description of the Prior Art

Blotting assays, including Western blots, Northern blots, and Southern blots, are powerful and widely used techniques in biological research for the identification and quantification of biological samples. These assays include first separating the sample components in gels by electrophoretic means, followed by transfer of the electrophoretically separated components from the gels to transfer membranes that are made of materials such as nitrocellulose, polyvinylidene fluoride (PVDF), or Nylon. Analytes can also be directly spotted on these supports or directed to specific regions on the supports by applying vacuum, capillary action, or pressure, without prior separation. The transfer membranes are then commonly subjected to a post-transfer treatment to enhance the ability of the analytes to be distinguished from each other and detected, either visually or by automated readers. When large numbers of transfer membranes are processed in this manner, or when the processing is performed repeatedly over time or by a succession of laboratory personnel, factors such as the cost of labor and time become significant, and variations from one procedure or one user to the next tend to introduce inconsistencies or result in incomplete treatments and other inaccuracies. Automated systems for these types of post-transfer and post-blotting treatments have therefore been developed, and examples are the FREEDOM ROCKER™ of Next Advance, Inc. (Avenill Park, N.Y., USA), the BLOTCYCLER™ of Precision Biosystems (Mansfield, Mass., USA), the HOEFER™ PROCESSOR PLUS™ of Amersham Biosciences (San Francisco, Calif., USA), and the BenchPro™ 4100 of Life Technologies (Carlsbad, Calif., USA).

SUMMARY OF THE INVENTION

The present invention resides in apparatus for treating a gel, slide, blotting membrane, or any such analyte support with one or more process fluids, the apparatus being particularly suitable for automated use, or for the processing of large numbers of such analyte supports simultaneously and under uniform conditions, or for the use of disposable components that are inexpensive to manufacture and simple to use. In one aspect, the invention resides in a plate and lid that when joined form a cavity in which an analyte support can be placed, and in certain embodiments a port or a penetrable or openable closure in the cavity for removing excess process fluid once the analyte support has been fully wetted or for otherwise separating the wetted support from the remaining fluid in the cavity. In certain embodiments of the invention, the cavity has an inclined floor. When process fluid is introduced into the cavity and the plate is rotated, the fluid travels up the inclined floor and across the sheet as the plate is rotated, then back down as the rotation is reduced or stopped. This cycle of intermittent rotation can be repeated a number of times to cause oscillating movement of the fluid across the analyte support in the radial direction relative to the axis of rotation. In other embodiments, the cavity has a horizontal floor, and in these embodiments as well as the inclined floor embodiments, the plate can be rotated back and forth, i.e., alternating clockwise with counterclockwise, to give a lateral oscillating movement for further distribution of the fluid across the analytes on the support. When a peripheral port is present for removal of excess fluid, certain embodiments also include a releasable closure over the port to prevent the escape of process fluid during the aforementioned cycling and yet to open and discharge the fluid when desired, for example by increasing the rotation rate of the plate to achieve a centrifugal force great enough to force the closure open. Various embodiments of the invention also include a variety of types of ports in the plate, the lid, or both, for the introduction of process fluid into the cavity, or for the retention of process fluid until its designated time of introduction, or for removing excess process fluid once the treatment is finished. Other aspects of the invention include methods for treating a blotting membrane or analyte support in general with one or more process fluids, by placing the analyte support on the floor of an enclosure cavity, adding the fluid(s) to the cavity, and rotating the enclosure to cause the fluid to travel radially or angularly (circumferentially), or both, along the analyte support, and doing this in an oscillating manner to wet the support with alternating forward and back flows of the fluid.

In certain embodiments of the invention, the plate is molded to form a segmented cavity to accommodate multiple analyte supports. The segments can be arranged for example as pie-shaped wedges around the center of the plate with one analyte support per wedge. In certain embodiments, these segments have sloping floors that collectively form an inverted cone sloping down toward the center of the plate with the plate's axis of rotation passing through the center. Two or more plates can be mounted to a common post, rack, or housing, to form a vertical stack which can be rotated for the simultaneous processing of analyte supports on all plates in the stack.

These and other features, variations, and uses of the invention will be apparent to those of skill in the art, some of which are shown in the attached figures and described below.

DETAILED DESCRIPTION OF EMBODIMENTS OF THE INVENTION

While the present invention is susceptible to a wide range of constructions and embodiments, an understanding of the central concepts and the invention as a whole can be gained from a detailed review of specific embodiments. One such embodiment is shown in the attached Figures.

Figure 1:
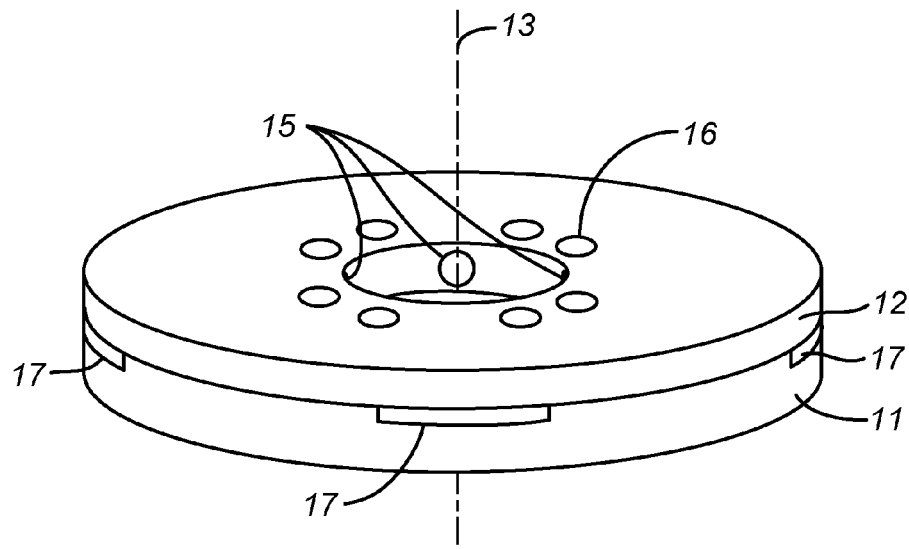
FIG. 1 is a perspective view of a plate and lid combination in accordance with the present invention.

FIG. 1 is a perspective view of a plate 11 and lid 12 joined together to form an enclosure. The plate and lid in this embodiment are both circular with a common axis 13 and each has a central opening, to allow access to the interior of the enclosure through septa 15. The central openings also accommodate an axial shaft (shown in a subsequent figure) to which the plate, or two or more such plates, can be mounted and about which the plate(s) can be rotated. Additional ports 16 for fluid introduction reside in the lid 12. The outer edge of the plate 11 has peripheral ports 17 that are either open or covered by closures that are capable of being opened by centrifugal force or other means.

Figure 2:
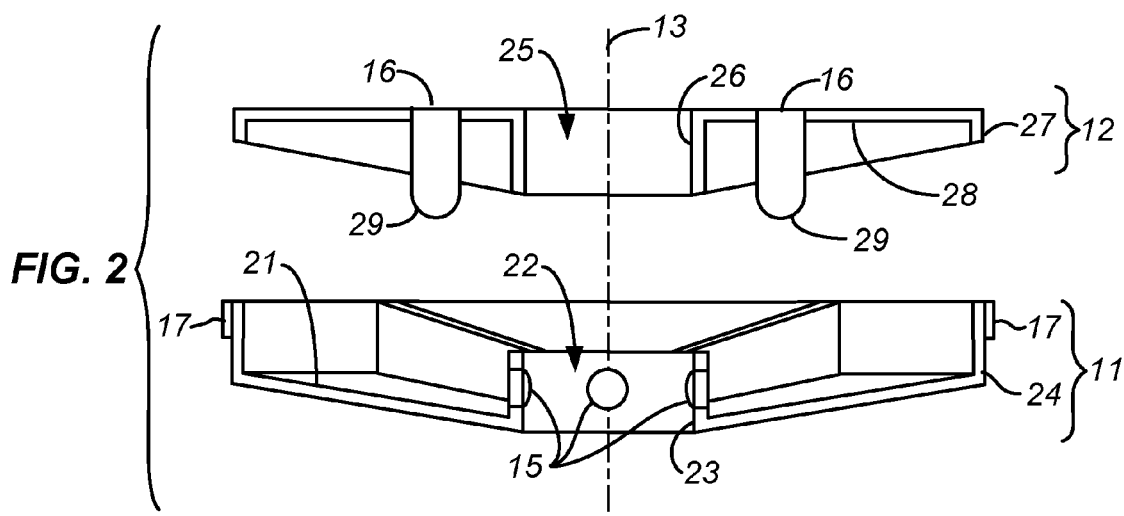
FIG. 2 is a vertical cross section of the plate and lid of FIG. 1.

FIG. 2 is a cross section of the plate 11 and lid 12 taken along a vertical plane passing through the axis 13, the plate and lid separated from each other for ease of viewing. The plate 11 has a floor 21 that is conical in shape, inclined downward toward the axis 13. The central opening 22 of the plate 11 is encircled by an internal circular wall 23, and another circular wall 24 runs along the outer periphery of the plate. The septa 15 are embedded in the internal circular wall 23. The lid 12 is coextensive with the plate and is securable to the plate by any conventional means, such as a snap fit, a clamp, a latch, or a threaded connection. The central opening 25 of the lid 12 is encircled by a circular wall 26 whose lower edge abuts the upper edge of the inner circular wall 23 of the plate when the lid and plate are joined, and an outer circular wall 27 runs along the outer periphery of the lid, abutting the outer circular wall 24 of the plate in the same manner as the inner circular walls. The lid is open at the bottom and, together with the plate which is open at the top, forms an enclosure when the two are joined. The enclosure has an internal cavity bounded at the base by the floor 21 of the plate, at the top by the ceiling 28 of the lid, and at the sides by the various circular walls 23, 24, 26, 27. The ports 16 in the lid are at the tops of wells 29 that are supported by the lid 12 and that protrude into the cavity between the plate 11 and the lid 12. The lower portions of the wells 29 are rupturable for reasons and by means described below.

Figure 3:
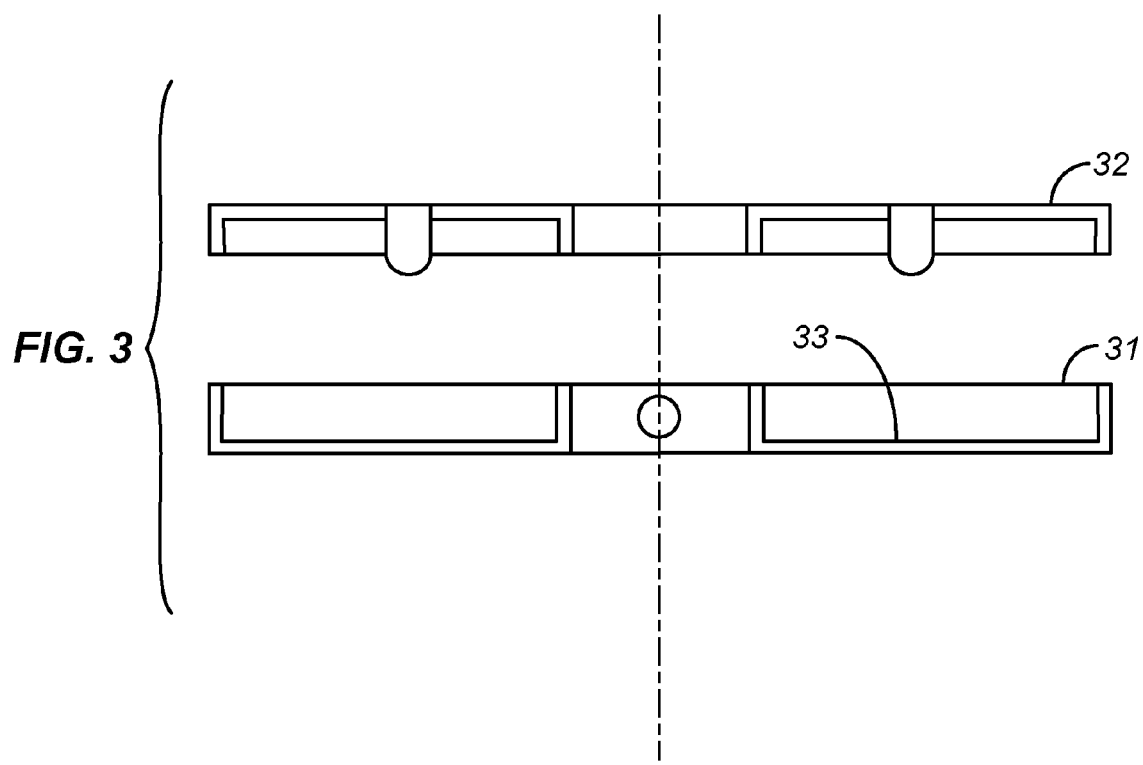
FIG. 3 is a vertical cross section of another plate and lid as alternatives to those of FIG. 1.

FIG. 3 is a cross section of an alternative plate 31 and lid 32, identical to those of FIG. 2 except with a planar (flat) floor 33.

Figure 4:
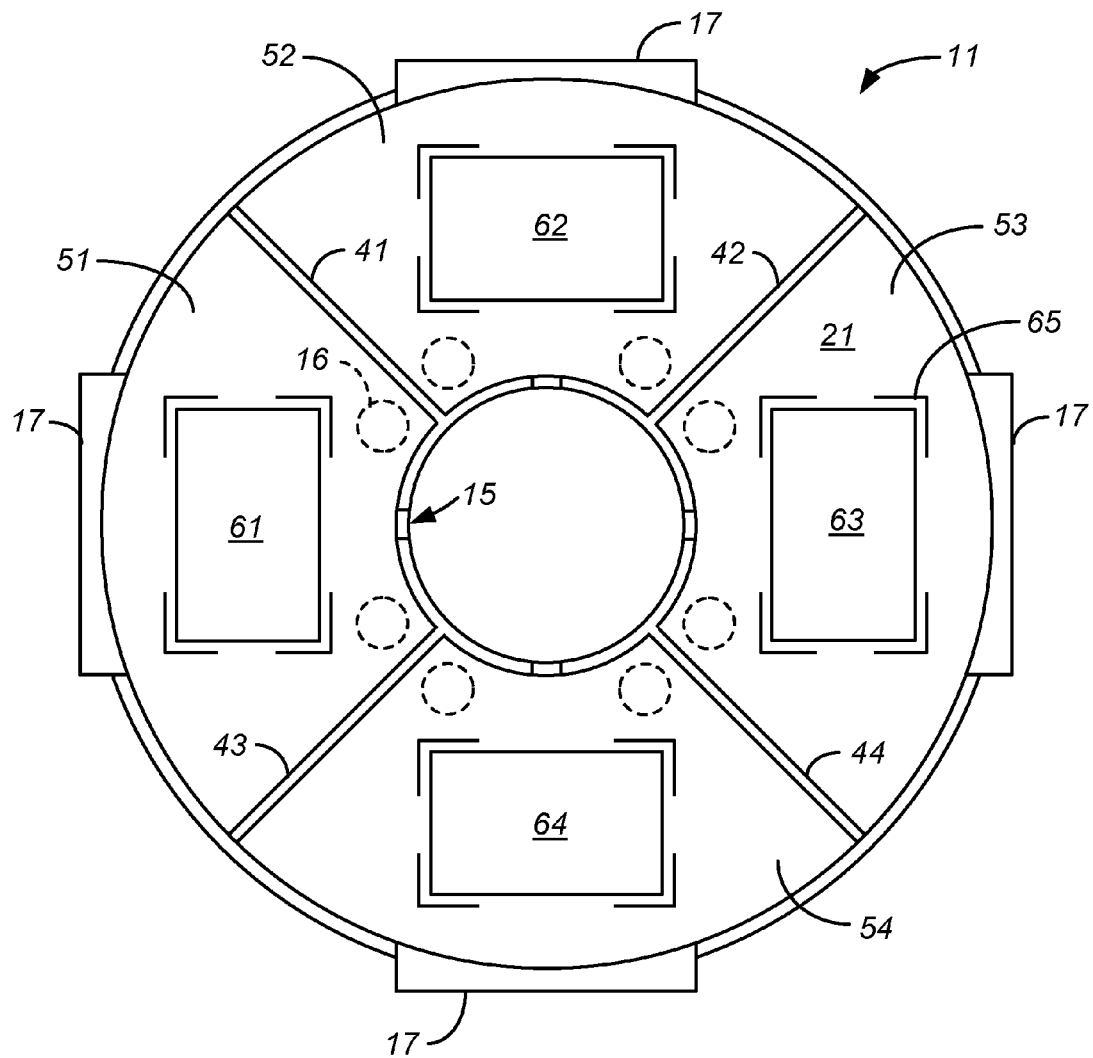
FIG. 4 is a top view of the plate of FIG. 1.

FIG. 4 is a top view of the plate 11 of FIG. 2. Extending up from the floor 21 of the plate are partitions 41, 42, 43, 44 that divide the plate into four sectors 51, 52, 53, 54. The sectors are thus truncated pie-shaped wedges. The partitions prevent exchange of fluid between the sectors, and thereby allow a procedure to be performed in any sector independently of the other sectors. To ensure that the partitions serve this function, the lid can have grooves formed in its undersurface to mate with the upper edges of the partitions. Each sector can accommodate a separate membrane 61, 62, 63, 64, or other analyte support, and corner guides 65 hold the membranes in place as the plates rotate and oscillate. Of the many variations that are possible within the scope of this invention, the number of sectors can be greater or lesser than that shown. The plate can thus be divided into six or eight sectors, for example, instead of four. The floor 21 of each sector is sloped downward toward the inner circular wall 23, and can also contain surface features that allow the flow of fluid beneath the membranes as well as over the upper surfaces of the membranes. These surface features may be ridges or bumps, for example, or a roughly textured surface. Four septa 15 are shown, one septum leading to each of the four sectors 51, 52, 53, 54, and communicating each sector with the central opening 22. Here as well, the number of septa is not critical and can vary, depending on the analyte support being processed and the procedure being performed. The septa can be pierced by syringe needles entering each septum from the central opening to deliver process fluids to each of the four sectors. The lid ports 16 are in the lid rather than the plate, but their locations are shown in this Figure in dashed lines. There are two lid ports 16 for each sector of the plate, or a total of eight lid ports in this embodiment. The reason for two lid ports for each sector is explained below, although this number can vary as well for the same reasons as the variability in the number of sectors and septa. The closures on the peripheral ports 17 can be mounted by spring-loaded hinges to hold these ports closed in the absence of external forces. The ports can thus be forced open, for example, by centrifugal force caused by rotation of the disk, and allowed to close when rotation stops. Open slits or mesh coverings can be used in place of the closures.

Figure 5:
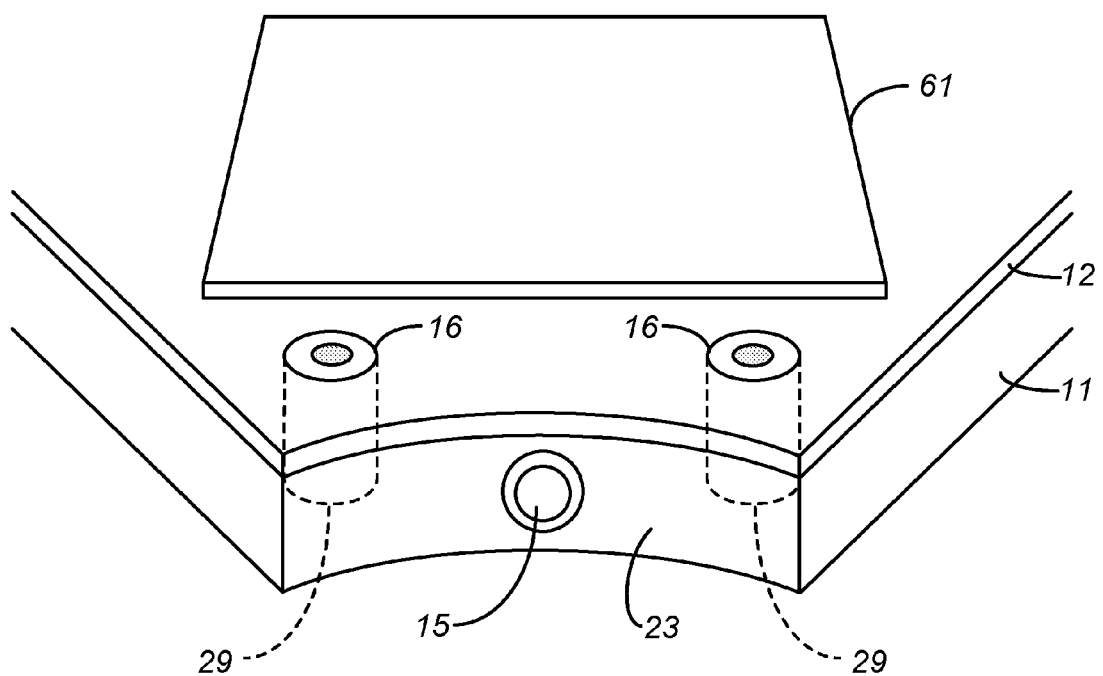
FIG. 5 is a perspective view of the inner end of one sector of the plate of FIG. 1 and the portion of the lid covering that sector.

FIG. 5 is a perspective view of portions of the plate 11 and lid 12 corresponding to one sector of the plate, as seen at an angle from above the central opening. A single septum 15 resides at the center of the section of the inner circular wall 23, and the two lid ports 16 lead to rupturable wells 29 (whose number can likewise vary for the reasons stated above) extending into the cavity above the sector. The lid ports 16 can be septa that are penetrable by needles similarly to the septum 15 in the inner circular wall 23, and the needles can extend through the rupturable wells to pierce the bottoms of the wells and release the well contents. Alternatively, the needles can supply pressurized air to cause the wells to burst and thereby release their contents. A further alternative are pins that are movably mounted to the lid ports and extend into the wells, the pins being movable by mechanical means or by air pressure to strike and rupture the bottoms of the wells. Other mechanisms for rupturing the wells to release their contents will be readily apparent to those skilled in laboratory equipment design and manufacture.

Figure 6:
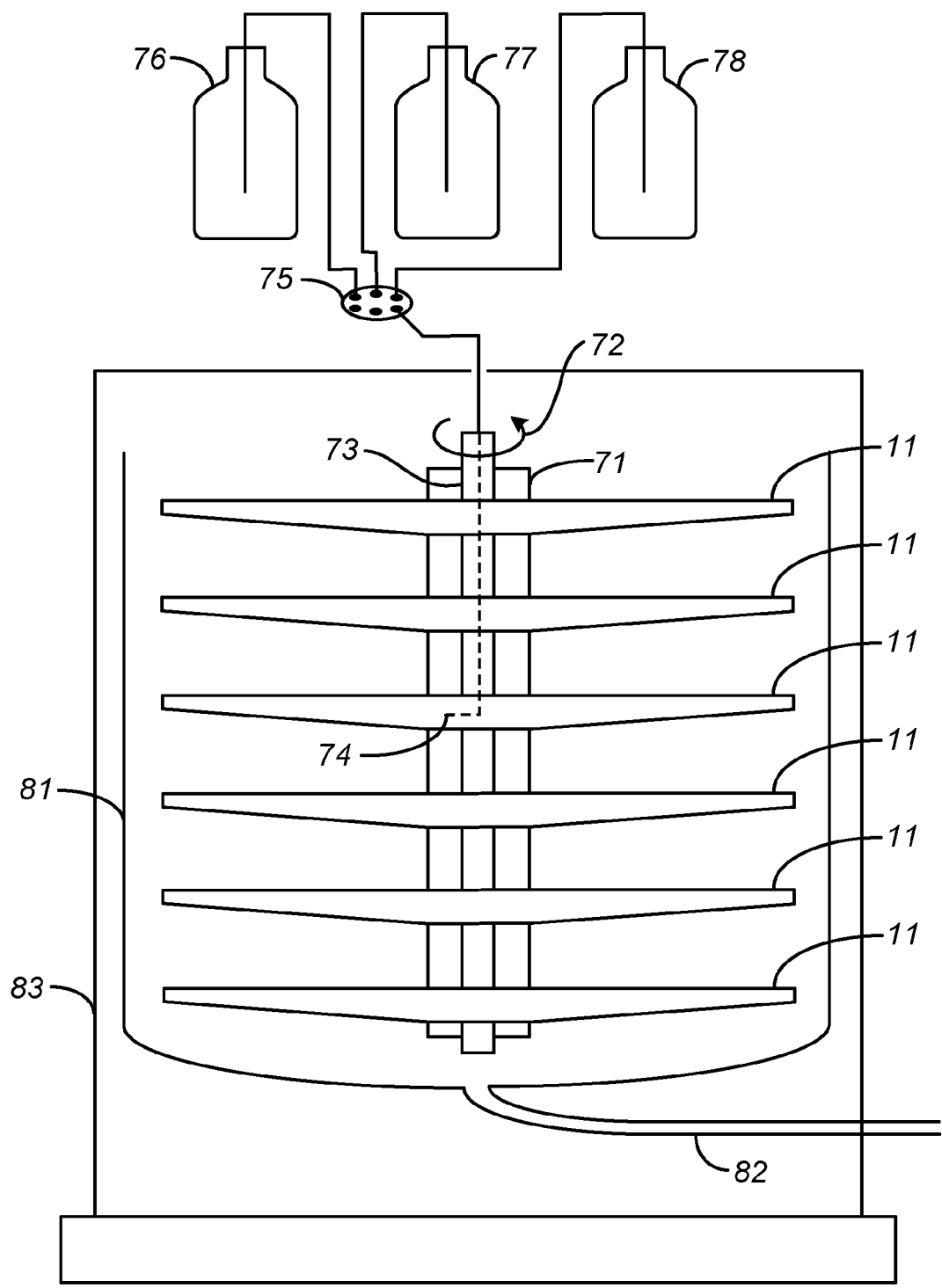
FIG. 6 is a diagram of a laboratory unit incorporating six plates of the type shown in FIG. 1.

FIG. 6 is a side view of an apparatus that includes a housing containing a rotatable rack holding six plates 11 with lids attached plus various supply vessels containing different process fluids, as well as conduits for directing the fluids to the plates and for collecting and removing used or excess fluids. The rack includes a central shaft 71 that supports the plates and that is rotatable by a multi-speed motor (not shown) in the direction indicated by the arrow 72. An axial tube 73 passes through the shaft. Within the axial tube is a movable needle 74 and at one end of the tube is a rotary valve 75 with ports connected to individual fluid supplies 76, 77, 78 and a pump (not shown) to deliver fluids to the plates. The needle 74 is mounted for movement up and down within the tube 73 and for insertion into and retraction from each plate. All such movements can be achieved and controlled by common mechanisms such as a gear and belt drive. The axial tube can also be connected to a pressurized air supply for functions involving the use of pressurized air. The plates 11 and supporting shaft 71 are surrounded by a tub 81 to receive the fluids that escape from the peripheral ports of the plates, the tub having a drain 82 to waste collection. The tub 81 is retained inside a housing 83 that can rest on a laboratory bench.

Although not shown in the drawings, the plates 11 and central shaft 71 can be equipped with structural features that maintain the spacing between adjacent plates, that secure the plates to the central shaft for purposes of controlling the rotation speed, and that hold the plates in position as the shaft rotates. A collar, for example, can extend upward from the top of each plate to allow the next higher plate to rest on the collar and thereby establish to vertical spacing. The collar can include a flange at its upper end that a user can grasp when the user is lowering the plate over the shaft inside the tub 81 or lifting the plate over the shaft and out of the tub after use.

Key-like structures can secure each plate or collar to the central shaft, including an indent in the lower surface of each plate or each collar and a series of pins, tabs, or similar protrusions extending from the shaft at periodically spaced heights along the shaft to engage the indents and thereby cause each plate to rotate with the shaft. The plates can contain bayonet mounts or other quick-connect mounts to join the plates to the shaft and to lock them in place with a small-angle turn. The top of the central shaft can be threaded and a threaded ring can be designed to engage this part of the shaft and to fit over the uppermost plate, thereby holding the plates in position. Any number of similar features can be readily envisioned by those of skill in the art.

The device and apparatus described above can be used for processing membranes obtained from a variety of samples, such as Southern blots, Northern blots, dot blots, and Western blots and any other analyte supports. With appropriately designed plates, the device can also be used for automating the process steps of other biological research techniques such as the staining and destaining of polyacrylamide gels. With changes to the number of sectors, guides, or both, the device can also be used to facilitate the staining or immunostaining of cells or microarrays on microscope slides. Other uses of the device will be apparent to those of skill in the art.

The treatment of a Western blot membrane is illustrative, and one example of a protocol that can be used for a group of Western blots using this apparatus is as follows.

Western blot membranes are placed in the various sectors of each of the plates 11, and the plates are closed by lids and mounted on the central shaft 71 which is then placed inside the tub 81 and housing 83. A blocking solution such as bovine serum albumin or nonfat milk in a solution of Tris or phosphate-buffered saline is then fed to the plates from one of the supply vessels 76 through the syringe needle 74 and the various septa 15. Motorized movement of the syringe needle 74 up and down the shaft 71 and in and out of the septa, together with incremental rotations of the shaft 71, allow the needle to inject the solution into all sectors in individual plates. The entire stack of plates is then rotated at a low speed to gently move the blocking solution up the slope of the plate floor toward the outer edges of each chamber sector by centrifugal force. After a short rotation time, rotation is halted to allow the solution to flow back down the slope of the floor, then resumed, and the process is repeated to achieve oscillating flow of the blocking solution over the membranes for a time sufficient to achieve the desired blocking. Once the programmed incubation period for the blocking is complete, the stack is rotated at a higher rate, one that produces a centrifugal force high enough to release or cause the closures on the peripheral ports 17 to open and release the blocking solution into the tub 81. The outer wall 24 of each plate helps to retain the membranes during the ejection of the blocking solution. A wash solution such as Tris-buffered saline Tween 20 (TBST) can then be fed in the same manner as the initial blocking solution, and the oscillating movement and subsequent release can be repeated for a prescribed time interval and iterations. If the membranes are initially dry, the blocking step can be preceded by injection of a wash solution, rotation of the plates to wet the membranes, and release of excess wash fluid. For PVDF membranes, an ethanol/methanol mixture can be used, followed by wash solution.

The two rupturable wells will have initially been charged with primary and secondary antibodies, respectively, and once the incubation with the blocking solution and any subsequent washing steps have been completed, a final charge of blocking solution or wash fluid can be placed in the sectors, and the mechanism for rupturing one of the wells in each sector of each plate is engaged. An example of such a mechanism is a specialized cap on the well pushed by a motorized arm to reach into the well and rupture its wall. The intermittent rotation of the disks is then resumed to incubate the western blot with the primary antibody in the same oscillating manner as the blocking solution. This is followed by a high-speed rotation to cause the plates to eject excess antibody solution from the peripheral ports. After performing additional washing steps in a similar manner, the well-rupturing mechanism is then applied to the second well to release the secondary antibody into the sectors for incubation with the western blots, followed by oscillating flow produced by intermittent plate rotation. This is likewise followed by a high-speed rotation to eject excess second antibody solution from the peripheral ports. In certain protocols, the first and second antibodies are combined in a single incubation. A typical protocol may include three washes between each antibody incubation, but any number of washes or incubations can be performed. Once the protocol is completed, the user can remove the plates from the apparatus and the lids from the plates so that the fully processed membranes can be recovered for imaging.

The plates can be made of a material that allows for direct imaging of the biological molecules on the membrane, or on support sheets in general such as gels or slides, without removing the support sheets from the plates. When such plates are used, a chemiluminescent substrate can be injected into each sector after the final wash steps to allow for antibody-specific detection of analytes on the sheets. Other imaging and detecting techniques can be used as well. The imaging system can for example be configured to detect analytes such as DNA, RNA, and proteins by methods involving ultraviolet, visible, fluorescent, or infrared light. System designs to accommodate these methodologies will be readily apparent to those of skill in the art. An imaging system to perform such detection can be incorporated into the apparatus. The entire process, with or without an incorporated imaging system, can be automated with a programmed sequence of movements of the injection needle and the motorized arms for rupturing the antibody wells, for selecting among different solutions to be injected, for starting and stopping the rotation of the plates, for selecting among different rotation speeds, and in some cases, for moving the plates up and down the shaft for easier access to the needle and well-rupturing mechanism, and all other functions served by the apparatus. The system can also contain a graphic user interface for programming protocols, manipulating protocols, and analyzing the results.

The plates can be disposable, i.e., inexpensively made and intended for a single use, and a blank plate can be used for purposes of washing the chamber 81 between uses. Plates can be marked with indicia such as bar codes for membrane identification. Examples of analyte supports that can be processed on the plates are small membranes measuring approximately 8 cm×8 cm, larger membranes measuring approximately 14 cm×9 cm, gels, and slides. In general, sheets of any sizes and dimensions or solid members of other geometries that can serve as analyte supports can be accommodated. The support can rest on the floor of the cavity or otherwise be supported in the cavity, such as by a rack in a vertical position.

As noted above, the apparatus and methods disclosed herein are useful in treating a wide variety of analyte supports bearing exposed analytes. Western blots are examples of such supports and the analytes that are retained on them. Western blotting is the transfer of proteins from electrophoretically-resolved biological samples to an immobilizing matrix on which the proteins are detected and identified, and often quantified. The techniques for electrophoretic separations of proteins and for transferring them to the immobilized phase are well known, described for example in *Techniques in Molecular Microbiology*, Walker, J. M., and W. Gaastra, eds. (MacMillan Publishing Company, 1983); and Bers, G., and D. Garfin, *Bio Techniques*, Vol. 3, No. 4, pp. 276-288 (1985). A prominent example of electrophoretic separation is polyacrylamide gel electrophoresis, and examples of blotting matrices are nitrocellulose, diazobenzyloxymethyl (DBM) and diazophenylthioether (DPT)-modified cellulose paper, and ion exchange papers such as diethylaminoethyl (DEAE) cellulose. Nitrocellulose is perhaps the most widely used. In the electrophoretic separation, the proteins migrate through the gel under the influence of an electric field at rates of migration that vary with the charge, size and shape of each protein. The separated proteins are then electrophoretically transferred from the gel to the blotting matrix.

Once transferred, the proteins are detected by conventional techniques. Examples of these techniques are those involving the use of antibody and various labeled materials such as an enzyme conjugate or a complex of colloidal gold with antibody. Nonspecific binding to the membrane can be avoided by the application of any of a variety of blocking agents to the membrane prior to transfer of the proteins and the binding of labeled antibody. One such blocking agent is the surfactant polyoxyethylene sorbitan monolaurate surfactant (TWEEN-20), which is commonly added in aqueous solution at a low concentration, such as 0.05% by weight.

Strips of nitrocellulose containing electrophoretically separated HIV-1 viral protein, for example, are commercially available for the detection of antibodies in the serum of an AIDS patient. In use, the strips are immersed in a solution of serum sample and labeled second antibody and mechanically agitated during incubation. Wash steps are normally required between incubations. The apparatus described herein is useful in performing these steps. A variety of label reagents have been used for anti-HIV immuno-blotting assays. Prominent among these are secondary antibodies for visualizing antigen-bound primary antibodies. Enzymes and gold-labeled secondary antibodies can also be used.

Southern blots and Northern blots are transfers of DNA and RNA, respectively, and here again, the methods of varied but well known. In a typical Southern blot, high-molecular-weight DNA strands are cut into fragments by the use of restriction endonucleases. The fragments are then separated according to size by electrophoresis on an agarose gel. A sheet of either nitrocellulose or nylon, serving as the analyte support, is then placed either on top of or below the gel to form a stack, and pressure is applied evenly to the stack, either using suction or by placing paper towels and a weight on top of the membrane and gel, to ensure uniform contact between gel and membrane. Capillary action moves the DNA from the gel onto the membrane where ion-exchange interactions bind the DNA to the membrane due to the negative charge of the DNA and positive charge of the membrane. The membrane is then baked in a vacuum or regular oven at 80° C. for 2 hours or exposed to ultraviolet radiation to permanently attach the transferred DNA to the membrane.

The membrane is then exposed to a hybridization probe—a single DNA fragment with a specific sequence whose presence in the target DNA is to be determined. The probe is labeled so that it can be detected, usually by incorporating radioactivity or being tagging with a fluorescent or chromogenic dye. In some cases, the probe may be made from RNA rather than DNA. Nonspecific binding of the probe to the membrane can be avoided by blocking the membrane surface with a blocking agent, examples of which are salmon or herring sperm DNA. Excess probe is then washed from the membrane, and the pattern of hybridization is visualized on X-ray film by autoradiography in the case of a radioactive or fluorescent probe, or in the case of a chromogenic label, by development of color on the membrane.

Southern blots performed with restriction enzyme-digested genomic DNA may be used to determine the number of sequences (gene copies, for example) in a genome. A probe that hybridizes only to a single DNA segment that has not been cut by the restriction enzyme will produce a single band on a Southern blot, whereas multiple bands will likely be observed when the probe hybridizes to several highly similar sequences, such as those that may be the result of sequence duplication. Modification of the hybridization conditions, such as by increasing the hybridization temperature or decreasing the salt concentration, for example, may be used to increase specificity and decrease hybridization of the probe to sequences that are less than 100% similar.

Southern blots can also be used for homology-based cloning on the basis of an amino acid sequence of the protein product of the target gene. To perform this procedure, oligonucleotides that are similar to the target sequence and radio-labeled are chemical synthesized, then used to screen a DNA library or other collections of cloned DNA fragments. Sequences that hybridize with the hybridization probe are further analyzed, for example, to obtain the full length sequence of the targeted gene. Because this technique starts with a protein and works backward to isolate the structural gene for that protein, it is called reverse genetics.

Southern blotting can also be used to identify methylated sites in particular genes. Particularly useful are the restriction nucleases MspI and HpaII, both of which recognize and cleave within the same sequence, HpaII only recognizing and cleaving methylated C's and MspI only recognizing and cleaving methylated DNA. Therefore, any methylated sites within a sequence analyzed with a particular probe will be cleaved by HpaII but not MspI.

Many of the procedures performed with the apparatus described herein involve sandwich assays, of which there are numerous variations. A forward sandwich assay, for example, is performed by immobilizing an unlabelled antibody on a solid substrate followed by placing the sample to be tested into contact with the immobilized antibody. After an incubation period sufficient to allow formation of an antibody-antigen complex, a second antibody that is specific to the antigen in the sample and is labeled with a reporter molecule capable of producing a detectable signal is then added and incubation proceeds for a time sufficient for the formation of another complex of antibody-antigen-labeled antibody. Any unreacted material is washed away, and the presence of the antigen is determined by observation of a signal produced by the reporter molecule. The results may either be qualitative, by simple observation of the visible signal, or quantitative, by comparing with a control ample containing known amounts of molecular marker. A variation on the forward assay is a simultaneous assay, in which both sample and labeled antibody are added simultaneously to the immobilizedantibody. The sample can be a cell extract, a tissue biopsy, serum, saliva, mucosal secretions, lymph, tissue fluid, respiratory fluid, or generally any biological sample. Alternatively, the sample can be fermentation fluid or supernatant fluid such as from a cell culture.

The support on which the initial antibody is immobilized in a sandwich assay can be glass or a polymer, the most commonly used polymers being cellulose, polyacrylamide, nylon, polystyrene, polyvinyl chloride or polypropylene. The support can be in the form of tubes, beads, discs, microplates, or any other surface suitable for conducting an immunoassay. The binding processes are well known in the art and generally consist of cross-linking, covalently binding or physical adsorption.

In an alternative method, the target molecules are immobilized in the biological sample and then exposed to specific antibody which may or may not be labeled with a reporter molecule. Depending on the amount of target and the strength of the reporter molecule signal, a bound target may be detectable by direct labeling with the antibody. In a still further alternative, the target-first antibody complex is exposed to a second labeled antibody that is specific to the first antibody, to form a target-first antibody-second antibody tertiary complex. This latter complex is then detected by the signal emitted by the reporter molecule.

The reporter molecule can be any molecule that, by its chemical nature, provides an analytically identifiable signal which allows the detection of antigen-bound antibody. Detection may be either qualitative or quantitative. Examples of types of reporter molecules useful in these assays are enzymes, fluorophores, radionuclide containing molecules (i.e., radioisotopes), and chemiluminescent molecules. Enzymes can be conjugated to the second antibody through glutaraldehyde or periodate, for example. Commonly used enzymes are horseradish peroxidase, glucose oxidase, β-galactosidase, and alkaline phosphatase. Substrates for these enzymes include those that produce a detectable color change upon hydrolysis by the corresponding enzyme. Fluorogenic substrates can also be used, fluorescing upon action of the enzyme rather than undergoing a color change. In all cases, the enzyme-labeled antibody is added to the first antibody-molecular marker complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually by spectrophotometric methods, to give an indication of the amount of molecular marker which was present in the sample. Alternatives to the reporter molecules discussed above are cell agglutination, such as red blood cells on latex beads, or inhibition of agglutination.

Fluorescent compounds such as fluorescein and rhodamine can be chemically coupled to antibodies without altering the binding capacity of the antibodies. When activated by illumination with light of a particular wavelength, the fluorochrome-labeled antibody adsorbs the light energy which induces a state of excitability in the molecule, which then causes emission of light energy at a characteristic color that is visually detectable with a light microscope. As in enzyme immunoassays, the fluorescent labeled antibody is allowed to bind to the first antibody-molecular marker complex. After unbound reagent is removed, the remaining tertiary complex is exposed to the excitation light of the appropriate wavelength, and the resulting fluorescence indicates the presence of the molecular marker of interest.

Many variations on the construction shown in the Figures and described above can be made without departing from the spirit and scope of the invention. Features shown in the plate can be placed in the lid, for example and those shown in the lid can be placed in the plate; the plate can have a shape other than circular; the peripheral ports can be closed by any of a wide variety of closures that are releasable by any conventional means in addition to the centrifugal force mentioned above; waste fluids can be removed from ports near the centers of the plates rather than from peripheral ports, either by gravity flow (in the case of plates with inclined floors) or by aspiration using needles and septa; and either the central shaft and fluid conduit or the plate stack can be moved vertically to access individual plates. Still further variations will be readily apparent to those skilled in the art.

In the claims appended hereto, the term "a" or "an" is intended to mean "one or more."

The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. A device for treating a solid member supporting an array of analytes with a process fluid, said device comprising:
   a circular plate and a circular lid, said plate and lid when joined forming one or more enclosure with a cavity therein, said cavity containing a solid member, said solid member being a blotting membrane,
   an inlet port for introducing fluid into said cavity,
   a support configured to rotate said plate and said lid about an axis perpendicular to said plate, said axis being centered in said plate and lid, and
   an outlet port on an outer edge of said plate relative to said axis, said outlet port for removing fluid from said cavity.

2. The device of claim 1 wherein said plate is planar.

3. The device of claim 1 wherein said cavity has a floor that is inclined downward toward said axis.

4. The device of claim 1 wherein said plate and lid each have central openings that are aligned when said plate and lid are joined, and said axis passes through said aligned central openings.

5. The device of claim 1 wherein said cavity is divided into a plurality of sectors symmetrically arranged about said axis, and said device comprises a plurality of peripheral ports on said outer edge of said plate, one peripheral port at a periphery of each said sector.

6. The device of claim 1 wherein said inlet port is a septum.

7. The device of claim 1 further comprising a releasable closure over said outlet port.

8. The device of claim 1 wherein said plate and lid have central openings that are aligned when said plate and lid are joined, said axis passes through said aligned central openings, and said device comprises a plurality of septa arranged around said aligned central openings with a separate septum leading to each of said sectors.

9. The device of claim 1, wherein said cavity comprises a septum and a rupturable well protruding into said cavity.

10. The device of claim 7, wherein said closure is opened by centrifugal force caused by rotation of said plate and closed when rotation of the device stops.

11. The device of claim 1, wherein the one or more cavity is wedged-shaped.

12. A method for treating an analyte support member supporting an array of analytes with a process fluid, said method comprising:
   (a) placing said member in the cavity of the device of claim 1, and injecting said process fluid into said cavity; and (b) intermittently rotating said cavity about the axis of rotation to cause said process fluid to travel back and forth across said member, thereby wetting said member with said process fluid; and (c) separating said wetted member from said process fluid, subsequent to said intermittent rotation, wherein said analyte support member is the blotting membrane.

13. The method of claim 12 wherein said cavity has a horizontal floor, and step (b) comprises causing said process fluid to travel back and forth across said member relative to said axis of rotation.

14. The method of claim 12 wherein said enclosed cavity has a floor that is inclined upward from said axis of rotation, and step (b) comprises causing said process fluid to travel radially back and forth across said floor.

15. The method of claim 12 wherein step (c) comprises ejecting said process fluid through said outlet port by centrifugal force.

16. The method of claim 12 wherein said enclosed cavity has a central opening surrounded by a wall, said axis of rotation passes through said central opening, and step (a) comprises injecting said process fluid into said cavity through a septum in said wall.

17. The method of claim 12 comprising treating a plurality of said analyte support members with process fluids, wherein said enclosed cavity is divided into a plurality of sectors symmetrically arranged about said axis of rotation, and step (a) comprises placing one of said members in each of said sectors.

18. The method of claim 12 wherein said enclosed cavity comprises a septum and a rupturable well protruding into said cavity, and step (a) comprises injecting a first process fluid into said cavity through said septum and releasing a second process fluid into said cavity by rupturing said rupturable well.

19. The method of claim 12 wherein said blotting membrane is a Western blot membrane.

20. The method of claim 12 wherein said blotting membrane is a Southern blot membrane.

21. The method of claim 12 wherein said blotting membrane is a Northern blot membrane.

22. The method of claim 12 wherein said blotting membrane is a dot blot membrane.

* * * * *